(12) United States Patent
Schwartz

(10) Patent No.: US 6,499,995 B1
(45) Date of Patent: Dec. 31, 2002

(54) PHOSPHORESCENT DENTAL APPLIANCE AND METHOD OF CONSTRUCTION

(76) Inventor: Dann A. Schwartz, 5504 Janice Ave., Kenner, LA (US) 70065

( * ) Notice: Subject to any disclaimer, the term of this patent is extended or adjusted under 35 U.S.C. 154(b) by 0 days.

(21) Appl. No.: 09/678,249

(22) Filed: Oct. 4, 2000

(51) Int. Cl.[7] ............................................. A61C 3/00
(52) U.S. Cl. ............................. 433/6; 264/21; 128/862
(58) Field of Search .......................... 433/29, 6, 140, 433/213; 128/848, 859, 861, 862; 264/21

(56) References Cited

U.S. PATENT DOCUMENTS

| | | | |
|---|---|---|---|
| 3,186,411 A | * | 6/1965 | Skidmore |
| 4,688,571 A | * | 8/1987 | Tesler |
| 5,487,662 A | * | 1/1996 | Kipke et al. .................. 433/37 |
| 5,692,894 A | | 12/1997 | Schwartz ....................... 433/6 |
| 5,692,895 A | * | 12/1997 | Farzin-Nia et al. ............ 433/8 |
| 5,718,577 A | * | 2/1998 | Oxman et al. ................ 433/37 |
| 5,829,980 A | * | 11/1998 | Sheridan et al. ............ 433/213 |
| 5,911,576 A | * | 6/1999 | Ulrich et al. ................. 433/68 |
| 6,068,475 A | * | 5/2000 | Stoyka, Jr. et al. ........... 433/80 |
| 6,095,146 A | | 8/2000 | Knauer ........................ 128/864 |
| 6,207,077 B1 | * | 3/2001 | Burnell-Jones ........ 252/301.36 |
| 6,244,269 B1 | * | 6/2001 | Tyler ........................... 128/859 |
| 6,299,441 B1 | * | 10/2001 | Novak |

* cited by examiner

*Primary Examiner*—Ralph A. Lewis
(74) *Attorney, Agent, or Firm*—John M. Harrison

(57) ABSTRACT

A glow-in-the-dark plastic dental appliance typically for pediatric dental patients, and method of constructing the appliance. According to a preferred method of the invention, the dental appliance is constructed by first forming an impression of a patient's upper or lower dentition and constructing a cast from the impression. The appliance is thermoformed over the cast, typically using a vacuum or pressure thermoforming machine and a sheet, plate or disc of thermoformable plastic impregnated or coated with a phosphorescent material. The appliance is capable of glowing in the dark for a limited period of time after exposure to a light source and as the appliance is worn on the patient's dentition, and is capable of repeated phosphorescence throughout the dental treatment period.

2 Claims, 2 Drawing Sheets

PHOSPHORESCENT DENTAL APPLIANCE AND METHOD OF CONSTRUCTION

BACKGROUND OF THE INVENTION

1. Field of the Invention

This invention relates to dental retainers or appliances for straightening and retaining teeth and more particularly, to a phosphorescent or glow-in-the-dark plastic dental appliance and method of construction, which appliance is particularly suitable for children. Using a vacuum or pressure thermoforming machine and a sheet, plate or disc of thermoformable plastic which is typically impregnated or coated with a phosphorescent material, the glow-in-the-dark appliance is vacuum-thermoformed over the dental impression cast and allowed to set on the cast. After removal from the cast, the appliance is capable of glowing in the dark for a limited period of time after exposure to a light source and as the appliance is worn on the patient's dentition. The appliance is capable of repeated phosphorescence throughout the dental treatment period.

2. Description of the Prior Art

A "Thermoformed Plastic Dental Retainer and Method of Construction" is described in my U.S. Pat. No. 5,692,894, dated Dec. 2, 1997. The dental retainer is constructed by first forming an impression of a patient's upper or lower dentition and constructing a cast from the impression. The retainer is vacuum thermoformed over the cast using a sheet, plate or disc of thermoformable plastic and a vacuum or pressure thermoforming machine. A protrusion or divot is formed in the retainer on the labial or lingual side of each tooth which is to be repositioned lingually or labially, respectively, and a gap, opening or window is formed in the retainer on the opposite side of the divot to accommodate unhindered tooth repositioning movement. As the retainer is worn on the patient's dentition over a period of days or weeks, the projecting divots apply pressure to the respective teeth and push the teeth into the gap or window of the retainer to a straightened position. By appropriately positioning the divots in the retainer with respect to the patient's malpositioned teeth, the teeth can be moved labially, lingually or rotated, as needed, for straightening.

My application Ser. No. 09/568,727 describes a "Thermoformed Plastic Dental Retainer and Method of Construction". The dental retainer is constructed by first forming an impression of a patient's upper or lower dentition and constructing a cast from the impression. The retainer is vacuum-thermoformed over the cast using a sheet, plate or disc of thermoformable plastic and a vacuum or pressure thermoforming machine. As the thermoformed plastic retainer sets on the cast, the retainer is rapidly cooled typically by spraying a refrigerant coolant on the retainer. This step causes the retainer to thermally contract against and precisely conform to the configuration and texture of the cast for an accurate and tight fit of the retainer on the patient's dentition.

U.S. Pat. No. 6,095,146, dated Aug. 1, 2000, to Knauer, et al., discloses "Glow-In-The-Dark Hearing Protective Devices", each including a semi-aural device, an earplug or an earmuff. A glow-in-the-dark material is incorporated into at least a part of the device such that the device emits light for an extended period of time in the dark after exposure to light. The glow-in-the-dark material can be disposed on a surface of the device or dispersed throughout the material which forms the device.

It is an object of the present invention to provide a glow-in-the-dark dental appliance and method of constructing the appliance.

Another object of the invention is to provide a glow-in-the-dark, thermoformed plastic dental appliance which is particularly suitable for children.

Still another object of the invention is to provide a thermoformed phosphorescent dental appliance and method of construction of the appliance including typically vacuum-thermoforming a sheet, plate or disc of phosphorescent plastic on a dental impression cast constructed from an impression of a typically pediatric patient's upper or lower dentition, and allowing the thermoformed appliance to set on the cast.

Yet another object of this invention is to provide a thermoformed plastic dental appliance and method of construction of the appliance, including initially forming an impression of a patient's upper or lower dentition and constructing a cast from the impression; vacuum or pressure-thermoforming the appliance over the cast using a vacuum or pressure thermoforming machine and a sheet, plate or disc of thermoformable plastic which is typically impregnated or coated with a phosphorescent material; and allowing the thermoformed plastic appliance to set on the cast, whereby the appliance is capable of glowing in the dark for a limited period of time after exposure to a light source and as the appliance is worn on the patient's dentition.

SUMMARY OF THE INVENTION

These and other objects of the invention are provided in a glow-in-the-dark thermoformed plastic dental appliance and method of construction. The dental appliance is constructed by first forming an impression of a typically pediatric patient's upper or lower dentition and constructing a cast from the impression. The appliance is thermoformed over the cast using a vacuum or pressure thermoforming machine and a sheet, plate or disc of thermoformable plastic impregnated or coated with a phosphorescent material. After the thermoformed plastic appliance sets on the cast, the appliance is removed from the cast and is capable of glowing in the dark for a limited period of time after exposure to visible light and as the appliance is worn on the patient's dentition, and is capable of repeated phosphorescence throughout the dental treatment period.

BRIEF DESCRIPTION OF THE DRAWINGS

The invention will be better understood by reference to the accompanying drawings, wherein.

DESCRIPTION OF THE PREFERRED EMBODIMENTS

Figure 1:
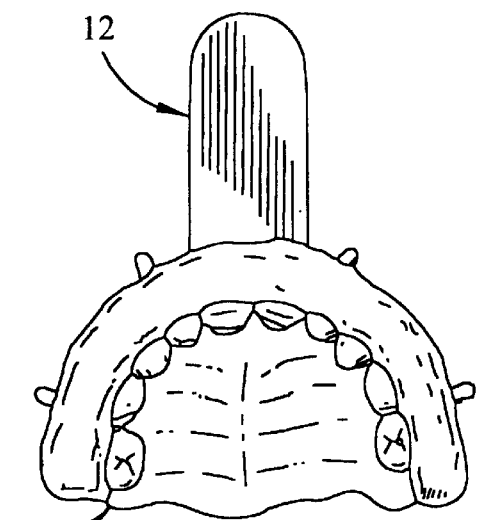
FIG. 1 is a top view of a patient's dental impression, formed in a standard or conventional dental impression tray.
Figure 2:
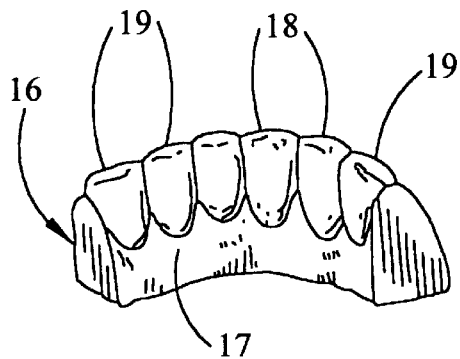
FIG. 2 is a perspective view of a dental impression cast formed from a dental impression, taken from the lower anterior dentition of a patient.
Figure 3:
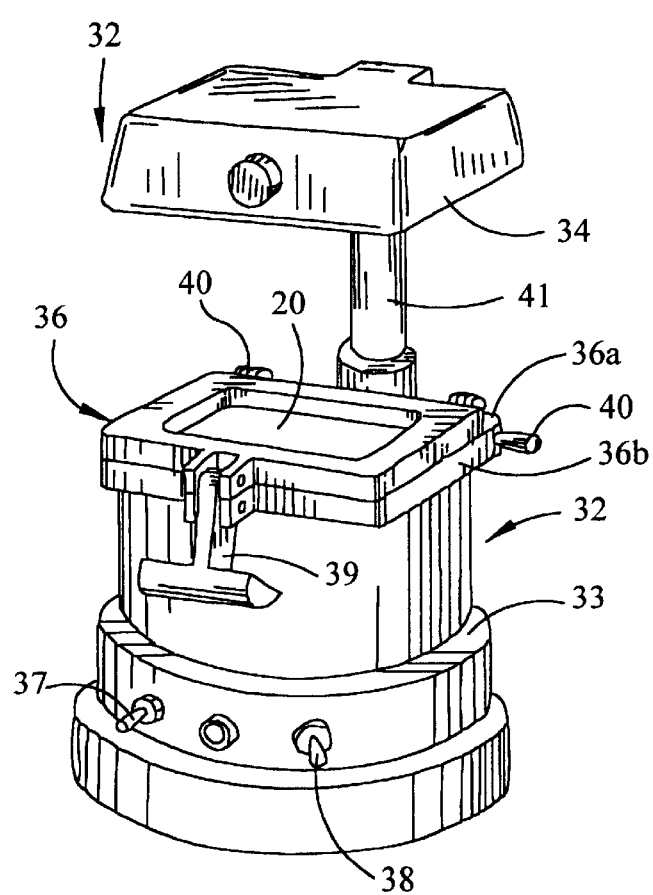
FIG. 3 is a perspective view of a typical standard or conventional vacuum thermoforming machine used in forming the phosphorescent dental appliance of this invention on a dental impression cast.
Figure 4:
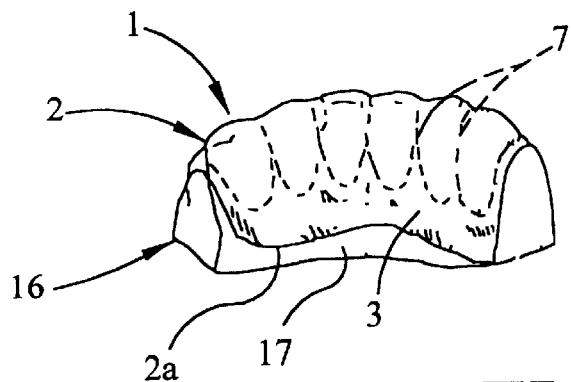
FIG. 4 is a perspective view of a preferred embodiment of a vacuum-thermoformed phosphorescent dental appliance, as the appliance sets on the dental impression cast.
Figure 6:
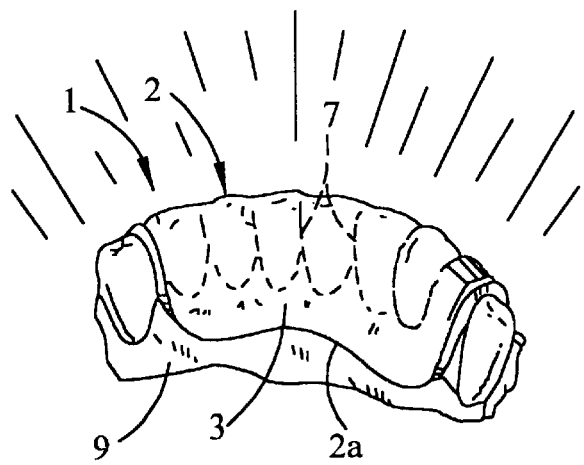
FIG. 6 is a perspective view of the phosphorescent dental appliance, worn a patient's lower dentition and more particularly illustrating phosphorescence of the appliance after exposure to a light source.

Referring initially to FIGS. 1–4 of the drawings, the phosphorescent dental appliance, hereinafter referred to as the appliance, of this invention is generally illustrated by reference numeral 1 in FIG. 4. The appliance 1 is characterized by an appliance body 2, thermoformed on a dental impression cast 16 (FIG. 2) from a sheet, plate or disc of thermoformable plastic material 20 (FIG. 3) which is impregnated or coated with a selected phosphorescent material, as hereinafter described. The dental impression cast 16 is formed from a conventional dental impression tray 12 shown in FIG. 1, using a pressure machine (not illustrated) or a conventional vacuum-thermoforming machine 32 (illustrated in FIG. 3), as hereinafter further described. The appliance body 2 is characterized by multiple tooth impressions 7, corresponding to the respective teeth of the patient's lower anterior dentition and illustrated in phantom in FIG. 4. The appliance body 2 includes a lingual surface 3, which, during appliance use, covers the lingual gingiva 9 of the dentition, as illustrated in FIG. 6, and a facial or labial surface, which covers the labial surface (not illustrated) of the dentition. The appliance body 2 is maintained in position on the patient's dentition by snugly engaging or "snapping into" the natural undercuts below the contact points of adjacent teeth, and may be removed as desired.

The thermoformable plastic sheet 20 is typically constructed of polyethylene or any other suitable thermoformable plastic, and a phosphorescent material such as copper-doped zinc sulfide (not illustrated) is typically interspersed throughout the plastic resin, according to the knowledge of those skilled in the art. Zinc sulfide is a well-known phosphorescent additive for plastic resins, and is commercially available from C. Withington, Co., Inc., under the trade name Excite 2330 LBY. The zinc sulfide pigment is added to the plastic resin typically in quantities greater than about 75% by weight of the pigment/plastic resin composition. However, it is understood that any concentration range of zinc sulfide which is sufficient to impart phosphorescence to the plastic sheet 20 after exposure of the plastic sheet 20 to a light source 25 (FIG. 5), can be used. Quantities of zinc sulfide as small as from about 3% to about 25% by weight of the pigment/plastic composition are known to be sufficient in imparting phosphorescence to plastic resins. Various thermoformable plastics which can be used in construction of the plastic sheet 20 include polyvinyl chloride (PVC), ABS plastic, polypropylene, polyethylene and polycarbonate, in non-exclusive particular. It is understood that the plastic sheet 20 can be impregnated with a variety of other phosphorescent additives such as zinc cadmium sulfide or alkaline earth sulfides, in non-exclusive particular, by methods which are well-known to those skilled in the art, to impart the desired phosphorescence of the plastic sheet 20 after exposure to a light source 25 (FIG. 5), as hereinafter described. It is further understood that instead of being interspersed throughout the plastic resin of the plastic sheet 20, the zinc sulfide or other phosphorescent material can be applied as a paint to one or both surfaces of the sheet 20 according to the knowledge of those skilled in the art.

Referring again to FIGS. 1–4 of the drawings, the appliance 1 is constructed by first making a dental impression 13 of the patient's upper or lower dentition, or both, a tooth or teeth of which dentition had been typically straightened using conventional orthodontic methods. The dental impression 13 is constructed preferably using a precision impression material such as polyvinyl siloxane and a standard or conventional dental impression tray 12, illustrated in FIG. 1. A dental impression cast 16 is then made from that portion of the dental impression 13 corresponding to the area of repositioned teeth, usually the anterior dentition, or that portion of the dentition extending from the left canine to the right canine, as illustrated in FIG. 2. The dental impression cast 16 includes a lingual surface 17, a labial surface (not illustrated) and cast teeth 18. Preparatory to forming the appliance 1, the dental impression cast 16 typically is dried thoroughly and trimmed such that the occlusal surfaces 19 of the cast teeth 18 have a slanted or tapered configuration, as further illustrated in FIG. 2, to facilitate easy removal of the appliance body 2 from the dental impression cast 16. Because the appliance 1 is maintained in position on the patient's dentition by "snapping into" the multiple undercuts below the contact points of adjacent teeth, the undercuts on the dental impression cast 16 may need trimming for augmentation if their presence on the dental impression cast 16 is not evident. As illustrated in FIG. 3, a standard or conventional pressure machine or a vacuum thermoforming machine 32, having a base 33 with a perforated top vacuum plate (not illustrated) and a heating unit 34 extending from the base 33 and mounted on a frame post 41 and energized by a heater switch 37, is used to vacuum-thermoform an appliance body 2 (FIG. 4) having tooth impressions 7 matching the cast teeth 18 of the dental impression cast 16. The vacuum thermoforming machine 32 also includes a slidable frame 36 having a top frame member 36a hinged to a bottom frame member 36b. The top frame member 36a is removably latched to the bottom frame member 36b by means of a frame latch knob 39. A vacuum motor (not illustrated) is contained in the base 33 and energized by a vacuum motor switch 38. Alternatively, a conventional pressure thermoforming machine (not illustrated) can be used to shape the appliance body 2 over the dental impression cast 16 according to the knowledge of those skilled in the art.

The appliance body 2 is formed on the dental impression cast 16 by first energizing the heating unit 34 of the vacuum thermoforming machine 32 by means of the heater switch 37. The dental impression cast 16 is then placed on the perforated vacuum plate (not illustrated) on the top of the base 33, with the cast teeth 18 of the dental impression cast 16 facing upwardly. Before the frame 36 is raised on the frame post 41 by means of frame lift knobs 40 to within a suitable heating distance of the heating unit 34, the top frame member 36a is pivoted upwardly with respect to the bottom frame member 36b. A thermoformable plastic sheet, disc or plate 20, typically constructed of polyethylene or other thermoformable plastic and impregnated with copper-doped zinc sulfide or any other suitable phosphorescent material, as heretofore described, is next centered on the bottom frame member 36b. The top frame member 36a is then pivoted downwardly and secured by means of the frame latch knob 39, and the frame 36 is raised on the frame post 41 such that the thermoformable plastic plate 20 is located immediately beneath the heating unit 34. After approximately 25 to 50 seconds, the thermoformable plastic plate 20 is heated to a suitable thermoforming temperature and typically begins to sag slightly, but should not be heated to a temperature such that it is allowed to sag about ½ inch or more. The vacuum motor in the base 33 is then energized by means of the vacuum motor switch 38, and the frame 36 is rapidly lowered on the frame post 41 over the vacuum plate of the base 33 by means of the frame lift knobs 40, such that the softened thermoformable plastic plate 20 is first draped and then tightly vacuum-pulled over the dental impression cast 16. After ten to fifteen seconds, the appliance body 2 has been formed from the thermoformable plastic plate 20, and the heating unit 34 is turned off. Immediately after thermoforming the appliance body 2 on the dental impression cast 16, the retentive proximal undercuts in the appliance body 2 can be enhanced, as needed, typically by using an ESSIX ACCENTUATOR (trademark) while the plastic appliance body 2 remains formable.

Figure 5:
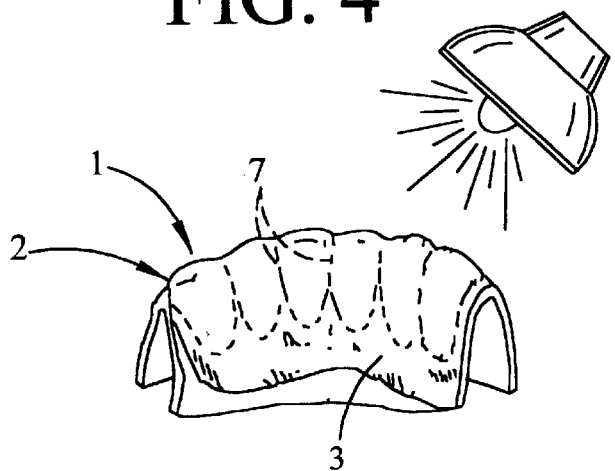
FIG. 5 is a perspective view of the phosphorescent dental appliance, removed from the dental impression cast and exposed to a light source.

As illustrated in FIG. 5, after the appliance body 2 is removed from the dental impression cast 16, the appliance body 2 can be exposed to a source of visible light 25 typically for a few minutes in order to activate the phosphorescent material impregnated in or coated on the appliance body 2. Accordingly, as illustrated in FIG. 6, for a limited period of time the appliance body 2 emits a phosphorescent glow which is particularly visible in the dark as the appliance body 2 is worn on the patient's dentition.

It will be appreciated by those skilled in the art that the phosphorescent dental appliance of this invention is capable of an accurate, tight and comfortable fit on a child patient's dentition during prolonged or short-term retention of straightened teeth and is suitable for repeated exposure to light and phosphoresence throughout the treatment period. The method of the invention can be used to construct phosphorescent retainers, mouth guards, splints and other dental appliances. While the material of choice for the dental impression is a precision impression material such as polyvinyl siloxane, it is understood that alginate can be used for the impression as long as the dental impression cast is poured within about 5 minutes of forming the impression. It is further understood that the thermoformable plastic sheet used to thermoform the appliance body can be any type of thermoformable plastic, including but not limited to polyvinyl chloride (PVC), ABS plastic, polypropylene, polyethylene and polycarbonate. Further, any type of phosphorescent material including copper-doped zinc sulfide, zinc cadmium sulfide or alkaline earth sulfides, in non-exclusive particular, can be used to impart phosphorescence to the plastic using methods which are well-known to those skilled in the art. Accordingly, it is understood that the phosphorescent material can be either interspersed throughout the plastic resin or painted on one or both surfaces of the thermoformable plastic sheets, as heretofore described and according to the knowledge of those skilled in the art.

While the preferred embodiments of the invention have been described above, it will be recognized and understood that various modifications can be made in the invention and the appended claims are intended to cover all such modifications which may fall within the spirit and scope of the invention.

Having described my invention with the particularity set forth above, what is claimed is:

1. A thermoformed phosphorescent dental appliance having an appliance body constructed by straightening a patient's dentition; making an impression of the patient's straightened dentition; constructing a dental impression cast from said impression; providing a sheet of thermoformable plastic, said sheet of thermoformable plastic having a selected phosphorescent material present in said sheet of thermoformable plastic in a quantity of greater than about 75% by weight of the phosphorescent/plastic composition; thermoforming said sheet of thermoformable plastic on said dental impression cast; and allowing said sheet of plastic to set on said dental impression cast and form said appliance body.

2. A method of constructing a phosphorescent dental appliance having an appliance body, comprising:

(a) straightening a patient's dentition;

(b) making an impression of the patient's dentition;

(c) constructing a dental impression cast of said impression;

(d) providing a sheet of thermoformable phosphorescent plastic having a selected phosphorescent material present in said sheet of thermoformable phosphorescent plastic in a quantity of greater than about 75% by weight of the phosphorescent/plastic composition;

(e) vacuum-thermoforming said sheet of plastic on said dental impression cast; and (f) allowing said sheet of plastic to set on said dental impression cast to form said appliance body, whereby said appliance body is capable of phosphorescence upon exposure of said appliance body to a source of light.

\* \* \* \* \*